Figure 1:
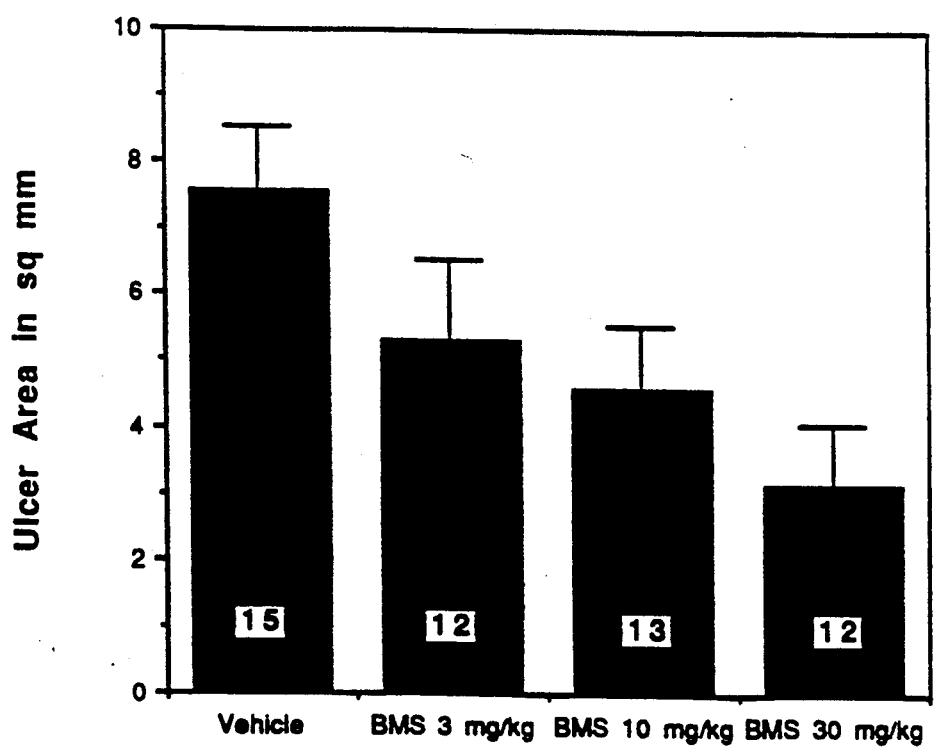

United States Patent [19]

Aberg et al.

[11] Patent Number: 5,262,419

[45] Date of Patent: Nov. 16, 1993

[54] METHOD FOR THE PROPHYLAXIS AND/OR TREATMENT OF ULCERATIVE GASTROINTESTINAL CONDITIONS USING A POTASSIUM CHANNEL ACTIVATOR

[75] Inventors: A. K. Gunnar Aberg, Lawrenceville, N.J.; Martin L. Ogletree; Eugene H. O'Keefe, both of Newtown, Pa.

[73] Assignee: E. R. Squibb & Sons, Inc., Princeton, N.J.

[21] Appl. No.: 897,217

[22] Filed: Jun. 11, 1992

[51] Int. Cl.$^5$ .......................................... A61K 31/505
[52] U.S. Cl. ...................... 514/275; 514/110; 514/302; 514/353; 514/355; 514/422; 514/456; 514/609; 514/925
[58] Field of Search .............. 514/275, 355, 422, 110, 514/302, 353, 456, 609, 925

[56] References Cited

U.S. PATENT DOCUMENTS

| | | | |
|---|---|---|---|
| 4,057,636 | 11/1977 | Petersen | 424/263 |
| 4,988,723 | 1/1991 | Shiokawa et al. | 514/394 |
| 5,011,837 | 4/1991 | Atwal et al. | 514/227.8 |
| 5,140,031 | 8/1992 | Atwal et al. | 514/392 |

FOREIGN PATENT DOCUMENTS

| | | |
|---|---|---|
| 205292 | 12/1986 | European Pat. Off. . |
| 214818 | 3/1987 | European Pat. Off. . |
| 274821 | 7/1988 | European Pat. Off. . |
| 344747 | 12/1989 | European Pat. Off. . |
| 358537 | 3/1990 | European Pat. Off. . |
| WO8700386 | 1/1987 | PCT Int'l Appl. . |

OTHER PUBLICATIONS

Chemical Abstracts 111:1233jm (1989).

*Primary Examiner*—Leonard Schenkman
*Attorney, Agent, or Firm*—Theodore R. Furman, Jr.; Ellen K. Park

[57] ABSTRACT

Ulcerative conditions of the gastro-intestinal tract, e.g., antiinflammatory-drug-induced ulcers, are treated or prevented by the administration of a potassium channel activator. Methods and combination products are also disclosed for the treatment of inflammatory conditions without causing ulceration of the gastrointestinal tract.

17 Claims, 1 Drawing Sheet

METHOD FOR THE PROPHYLAXIS AND/OR TREATMENT OF ULCERATIVE GASTROINTESTINAL CONDITIONS USING A POTASSIUM CHANNEL ACTIVATOR

FIELD OF THE INVENTION

The present invention relates to a method for protecting against and/or treating ulcerative gastrointestinal conditions, including anti-inflammatory-drug-induced ulcers, employing a potassium channel activator (PCA), as well as to compositions, combinations and improved methods for treating inflammatory conditions.

BACKGROUND OF THE INVENTION

Anti-inflammatory drugs, such as aspirin, indomethacin, ibuprofen, meclofenamate, naproxen, phenylbutazone, piroxicam and various corticosteroids are effective in treating or controlling pain, including headache, and in decreasing joint swelling, tenderness, pain and stiffness in conditions such as rheumatoid arthritis. Unfortunately, although such anti-inflammatory drugs are effective in treating pain and inflammatory conditions, they cause development of gastrointestinal ulcers thereby seriously limiting chronic use of these drugs.

DESCRIPTION OF THE INVENTION

In accordance with the present invention, it has now been found that gastrointestinal ulcers are effectively treated using a therapeutic amount of a potassium channel activator (PCA). Additionally, it has been found that the incidence of antiinflammatory drug-induced gastric ulcers is substantially reduced when PCA's are administered with the antiinflammatory drug. Thus, PCA s can be used prophylactically in patients taking antiinflammatory drugs. This can be accomplished by administering a single combination dosage form or by the concomitant administration of a PCA and an antiinflammatory drug. Accordingly, combination products and improved methods of treating inflammation are also provided by the present invention.

Any PCA can be used in the methods and compositions of the present invention. Preferably, PCA's which have little or no vasodilator activity in normal tissue, but which show an anti-ischemic effect in ischemic tissue, are preferred.

Suitable potassium channel activators include those disclosed in U.S. Pat. No. 4,057,636, especially the compound

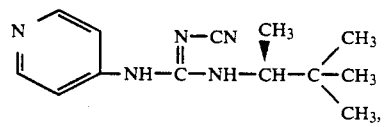

known as pinacidil; those disclosed in European Patent Application 0 274 821, especially the compound

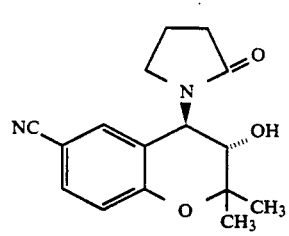

known as cromakalim; nicorandil; minoxidil; compounds in copending application U.S. Ser. No. 661,763 filed Feb. 27, 1991 having the formula

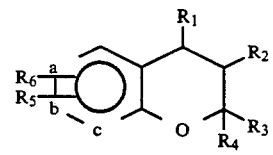

wherein a, b, and c are all carbons or one of a, b and c can be nitrogen or —NO— and the others are carbons;

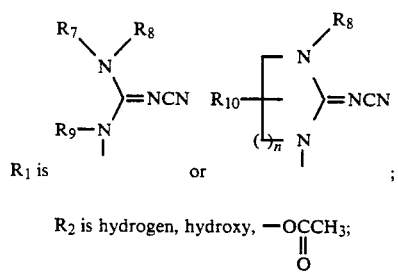

$R_2$ is hydrogen, hydroxy, —OCCH$_3$;
$\overset{\parallel}{O}$ $R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl, N

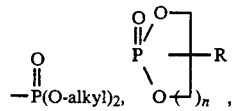

halogen, amino substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

$R_6$ is selected from H, alkyl, OH, O-alkyl, amino, substituted amino, CN, and NO$_2$;

$R_7$ and $R_8$ are each independently selected from hydrogen, alkyl, alkenyl, aryl (including phenyl substituted with R' and R" as defined below), (heterocyclo)alkyl, heterocyclo, arylalkyl, cycloalkyl and (cycloalkyl)alkyl, substituted alkyl wherein the substituents include alkoxy, alkylthio and substituted amino, or $R_7$ and $R_8$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R_9$ and $R_{10}$ are selected from hydrogen, alkyl, alkenyl, aryl, arylalkyl, cycloalkyl or cycloalkyl; and n is 1, 2 or 3; with the compound (where R' and R" are independently hydrogen, cyano, alkyl, alkoxy, nitro, hydroxy, halo, haloalkyl, alkylthio, amino, —N(alkyl)$_2$, —NHalkyl or benzyloxy with the proviso that at least one of R' and R" is other than hydrogen) being preferred;

compounds in copending application U.S. Pat. No. 5,011,837 granted Apr. 30, 1991 having the formula and its possible tautomers and wherein $R_1$ is alkyl, alkenyl, alkynyl, haloalkyl, cycloalkyl, aryl, arylalkyl or cycloalkylalkyl;

$$R_2 \text{ is } -C\equiv N, -NO_2, -\overset{O}{\underset{\|}{C}}R_5, -\overset{O}{\underset{\|}{C}}-OR_5, -\overset{O}{\underset{\|}{C}}\text{-amino},$$

$$-\overset{O}{\underset{\|}{C}}\text{-substituted amino, } CF_3 \text{ or } -\overset{(O)_m}{\underset{\|}{S}}-R_1;$$

$R_3$ and $R_4$ are each independently selected from —$R_2$, hydrogen, alkyl, alkenyl, alkynyl, haloalkyl, halo, alkoxy, —NHalkyl, —N-(alkyl)$_2$, —S-alkyl, —O-arylalkyl, —S-arylalkyl or —S-aryl, —O-aryl, —NHarylalkyl, or $R_2$ and $R_3$ taken together are a group which forms a ring with the two carbon atoms to which they are attached, which group is selected from $$-\overset{(O)_m}{\underset{\|}{S}}-(CH_2)_n-CH_2-, \quad -\overset{O}{\underset{\|}{C}}X(CH_2)_pCH_2-,$$

$$-\overset{O}{\underset{\|}{C}}-CH_2(CH_2)_pX-;$$

wherein
m=1 or 2;
n=1-3;
p=0-2;
X is O, NR$_5$, CH$_2$; and,
R$_5$ is hydrogen or R$_1$;

compounds disclosed in copending patent application Ser. No. 776,921 filed Oct. 15, 1991 of the formula wherein A can be —CH$_2$—, —O—, —NR$_9$—, —S—, —SO— or —SO$_2$—, where R$_9$ is hydrogen or lower alkyl of 1 to 4 carbons;

wherein X is oxygen or sulfur;

$$Y \text{ is } -NR_8, -O-, -S- \text{ or } -\overset{R_{10}}{\underset{|}{C}H}-;$$

R$_1$ is aryl, arylalkyl, heterocyclo or (heterocyclo)alkyl;

R$_2$ is hydrogen, hydroxy, $$-\overset{}{\underset{\|}{O}}\overset{}{C}CH_3;$$

R$_3$ and R$_4$ are each independently hydrogen, alkyl or arylalkyl, or, R$_3$ and R$_4$ taken together with the carbon atom to which they are attached form a 5- to 7-membered carbocyclic ring;

R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl, $$-\overset{O}{\underset{\|}{P}}(O\text{-alkyl})_2, \quad \overset{O}{\underset{\|}{\overset{}{P}}}\overset{O}{\underset{\backslash}{\overset{/}{}}}\overset{}{\underset{}{O}}\overset{}{\underset{}{\leftarrow}})_n,$$

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

R$_6$ is selected from H, alkyl, halo, OH, O-alkyl, amino and substituted amino;

R7 and R8 are each independently selected from hydrogen, alkyl, arylalkyl;
n is 1, 2 or 3; and,
R10 is hydrogen, hydroxy, alkyl or O-alkyl; and compounds in U.S. copending application Ser. No. 745,563 filed Aug. 15, 1991 having the general formula

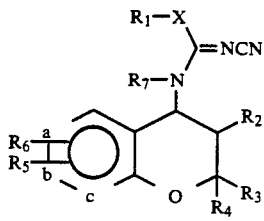 F wherein a, b and c are all carbons or one of a, b and c can be nitrogen or —NO— and the others are carbons; where X is oxygen or sulfur;
R1 is selected from aryl, arylalkyl, (heterocyclo)alkyl, heterocyclo, cycloalkyl and (cycloalkyl)alkyl;
R2 is hydrogen, hydroxy,

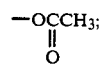

R3 and R4 are each independently hydrogen, alkyl or arylalkyl, or R3 and R4 taken together with the carbon atom to which they are attached form a 5- to 7-membered carbocyclic ring;
R5 is selected from H, alkyl, haloalkyl, alkenyl, alkynyl, cycloalkyl, arylalkyl, cycloalkylalkyl, —CN, —NO2, —COR, —COOR, —CONHR, —CONR2, —CF3, S-alkyl, —SOalkyl, —SO2alkyl,

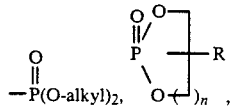

halogen, amino, substituted amino, O-alkyl, OCF3, OCH2CF3, —OCOalkyl, —OCONRalkyl, —NRCOalkyl and NRCOOalkyl, NRCONR2 wherein R in each of the above groups can be hydrogen, alkyl, aryl, arylalkyl, cycloalkyl, or (cycloalkyl)alkyl;
R6 is selected from H, alkyl, OH, O-alkyl, amino, substituted amino, CN and NO2;
R7 is selected from hydrogen, alkyl, alkenyl, aryl, arylalkyl, cycloalkyl or cycloalkylalkyl; and,
n is 1, 2 or 3; and,
compounds disclosed in copending application Ser. No. 630,472 filed Dec. 19, 1990 having the formula

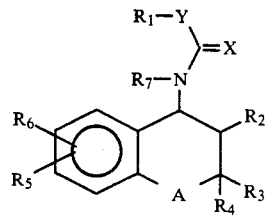 G wherein A can be —CH2—, —O—, —NR9—, —S—, —SO— or —SO2—, where R9 is hydrogen or lower alkyl of 1 to 4 carbons;
wherein X is oxygen or sulfur;
Y is —NR8, —O—, —S— or

R1 is aryl, arylalkyl, heterocyclo or (heterocyclo)alkyl;
R2 is hydrogen, hydroxy,

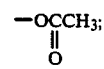

R3 and R4 are each independently hydrogen, alkyl or arylalkyl, or R3 and R4 taken together with the carbon atom to which they are attached form a 5- to 7-membered carbocyclic ring;
R5 is selected from H, alkyl, haloalkyl, alkenyl, alkynyl, cycloalkyl, arylalkyl, cycloalkylalkyl, —CN, —NO2, —COR, —COOR, —CONHR, —CONR2, —CF3, S-alkyl, —SOalkyl, —SO2alkyl,

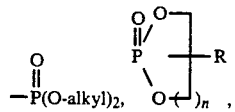

halogen, amino, substituted amino, O-alkyl, OCF3, OCH2CF3, —OCOalkyl, —OCONRalkyl, —NRCOalkyl and NRCOOalkyl, NRCONR2 wherein R in each of the above groups can be hydrogen, alkyl, aryl, arylalkyl, cycloalkyl, or (cycloalkyl)alkyl or haloalkyl;
R6 is selected from H, alkyl, halo, OH, o-alkyl, amino and substituted amino, O-alkyl, OCOalkyl, OCONRalkyl, NRCOalkyl and NRCOOalkyl, NRCON(R)2 wherein R in each of the above groups can be hydrogen, alkyl, aryl, arylalkyl, cycloalkyl, (cycloalkyl)alkyl or haloalkyl;
R7 and R8 are each independently selected from hydrogen, alkyl, arylalkyl;
or R1 and R8, or R1 and R7, or R7 and R8 taken together can form a 5- to 7-membered saturated or unsaturated ring, which may further include an aryl group fused to 2 carbon atoms of such 5- to 7-membered ring;
n is 1, 2 or 3; and,
R10 is hydrogen, hydroxy, alkyl or O-alkyl.
Also suitable for use herein are compounds as disclosed in U.S. Pat. No. 4,988,723 granted Jan. 29, 1991 having the formula

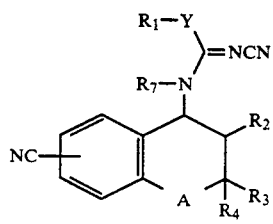 H wherein $R^1$ and $R^2$ are each lower alkyl;
$R^3$ is hydroxy or acyloxy and $R^4$ is hydrogen or
$R^3$ and $R^4$ are linked together to form a bond, and
(i) Y is —S—, —O— or a group of the formula:

wherein $R^7$ is hydrogen, acyl or lower alkyl which may have suitable substituent(s), and
$R^5$ and $R^6$ are each hydrogen or lower alkyl,
(ii) Y is as defined above, and $R^5$ and $R^6$ are linked together to form lower alkylene, or
(iii) Y-$R^5$ is a heterocyclic group which may have suitable substituent(s), and $R^6$ is hydrogen or lower alkyl compounds as disclosed in EP 214,818 having the formula

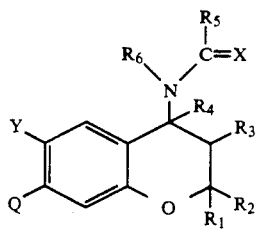

J and salts thereof, wherein
one of $R_1$ and $R_2$ is hydrogen or $C_{1-4}$alkyl and the other is $C_{1-4}$alkyl or $R_1$ and $R_2$ together are $C_{2-5}$-polymethylene;
either $R_3$ is hydrogen, hydroxy, $C_{1-6}$alkoxy or $C_{1-7}$acyloxy and $R_4$ is hydrogen or $R_3$ and $R_4$ together are a bond;
$R_5$ is hydrogen, $C_{1-6}$alkyl optionally substituted by halogen, hydroxy, $C_{1-6}$alkoxy, $C_{1-6}$alkoxycarbonyl, carboxy or amino optionally substituted by one or two independent $C_{1-6}$alkyl groups, or $C_{2-6}$alkenyl, amino optionally substituted by a $C_{1-6}$alkyl or $C_{1-6}$alkenyl group or by a $C_{1-6}$alkanoyl group optionally substituted by up to three halo atoms, by a phenyl group optionally substituted by $C_{1-6}$alkyl, $C_{1-6}$alkoxy or halogen, or aryl or heteroaryl, either being optionally substituted by one or more groups or atoms selected from the class of $C_{1-6}$alkyl, $C_{1-6}$alkoxy, hydroxy, halogen, trifluoromethyl, nitro, cyano, $C_{1-12}$carboxylic acyl, or amino or aminocarbonyl optionally substituted by one or two $C_{1-6}$alkyl groups and $R_6$ is hydrogen or $C_{1-6}$alkyl, or $R_5$ and $R_6$ together are —CH$_2$—(CH$_2$)$_n$—Z—(CH$_2$)$_m$— wherein m and n are 0 to 2 such that m+n is 1 or 2 and Z is CH$_2$, O, S or NR wherein R is hydrogen, $C_{1-9}$alkyl, $C_{2-7}$alkanoyl, phenyl $C_{1-4}$alkyl, naphthylcarbonyl, phenylcarbonyl or benzylcarbonyl optionally substituted in the phenyl or naphthyl ring by one or two of $C_{1-6}$alkyl, $C_{1-6}$alkoxy or halogen; mono- or bi-cyclic-heteroarylcarbonyl;
X is oxygen or sulphur;
Y and Q are electron withdrawing groups; and
the nitrogen-containing group in the 4-position being trans to the $R_3$ group when $R_3$ is hydroxy, $C_{1-6}$alkoxy or $C_{1-7}$acyloxy;

compounds as disclosed in EP 359,537 having the formula

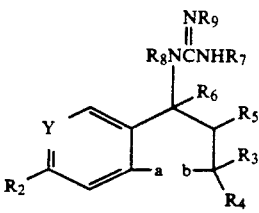

K wherein
a and b together form an —O— or —CH$_2$— linkage or a bond;
either Y is N and $R_2$ is hydrogen; or
Y is C-$R_1$;
wherein
either one of $R_1$ and $R_2$ is hydrogen and the other is nitro, cyano, halo, $CF_3$, formyl, aldoxime, $CF_3O$. $NO_2$—CH=CH—, NC—CH=CH—;
a group $R_xX$-wherein $R_x$ is $C_{1-6}$alkyl, aryl or heteroaryl either of which may be optionally substituted by one, two or three of $C_{1-4}$alkyl, $C_{1-4}$alkoxy, nitro, halo, $CF_3$ and cyano; and X is C=O, O.C=O, C=O.O, CHOH, SO, SO$_2$, O.SO, O.SO$_2$, CONH, O.CONH, C=S, O.C=S, C=S.O, CH.SH, SONH, SO$_2$NH, O.SONH, O.SO$_2$NH, CO—CH=CH, C=NHOH, C=NNH$_2$;
or a group $R_yR_zNZ$— wherein $R_y$ and $R_z$ are independently hydrogen or $C_{1-6}$alkyl and Z is C=O, SO or SO$_2$; or
$R_1$ is a $C_{3-8}$cycloalkyl group or a $C_{1-6}$alkyl group optionally substituted by a group which is hydroxy, $C_{1-6}$alkoxy, amino optionally substituted by one or two $C_{1-6}$alkyl groups, $C_{1-7}$alkanoylamino, $C_{3-8}$cycloalkyloxy or $C_{3-8}$cycloalkylamino; and $R_2$ is hydrogen; or
one of $R_1$ and $R_2$ is nitro, cyano or $C_{1-3}$alkylcarbonyl and the other is a different group selected from nitro cyano, halo, $C_{1-3}$alkylcarbonyl, methoxy or amino optionally substituted by one or two $C_{1-6}$alkyl or by $C_{2-7}$alkanoyl;
either one of $R_3$ and $R_4$ is hydrogen or $C_{1-4}$alkyl and the other is $C_{1-4}$alkyl; or
$R_3$ and $R_4$ together are $C_{2-5}$polymethylene;
either $R_5$ is hydrogen, hydroxy, $C_{1-6}$alkoxy or $C_{1-7}$acyloxy; and
$R_6$ is hydrogen; or
$R_5$ and $R_6$ together are a bond;
either $R_7$ is hydrogen, $C_{1-6}$alkyl, $C_{3-6}$cycloalkyl, $C_{2-6}$alkenyl or $C_{2-6}$alkynyl; and
$R_8$ is hydrogen or $C_{1-6}$alkyl; or
$R_7$ and $R_8$ together are $C_{2-4}$polymethylene;
$R_9$ is CN, NO$_2$, COR$_{10}$ wherein $R_{10}$ is $C_{1-3}$alkyl, NH$_2$, NH($C_{1-3}$alkyl), $CF_3$ or phenyl optionally substituted as defined for $R_x$; and
the $R_8N(NR_9)NHR_7$ moiety is trans to the $R_5$ group when $R_5$ is hydroxy, $C_{1-6}$alkoxy or $C_{1-7}$acyloxy;

compounds as disclosed in EP 205,292 having the formula

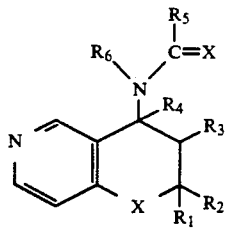

L wherein
one of $R_1$ and $R_2$ is hydrogen or $C_{1-4}$alkyl and the other is $C_{1-4}$alkyl or $R_1$ and $R_2$ together are $C_{2-5}$-polymethylene;

either $R_3$ is hydrogen, hydroxy, $C_{1-6}$alkoxy or $C_{1-6}$acyloxy and $R_4$ is hydrogen or $R_3$ and $R_4$ together are a bond;

$R_5$ is hydrogen; $C_{1-6}$alkyl optionally substituted by up to three halo atoms, by hydroxy, $C_{1-4}$alkoxy, $C_{1-6}$alkoxycarbonyl, carboxy, or amino optionally substituted by one or two independent $C_{1-6}$alkyl groups or disubstituted by $C_{4-5}$polymethylene, $C_{2-6}$alkenyl; amino optionally substituted by a $C_{1-6}$alkyl or $C_{1-6}$alkenyl group or by a $C_{1-6}$alkanoyl group optionally substituted by up to three halo atoms, by a phenyl group optionally substituted by $C_{1-6}$alkyl, $C_{1-6}$alkoxy or halogen; or aryl or heteroaryl, either being optionally substituted by one or more groups or atoms selected from the class of $C_{1-6}$alkyl. $C_{1-6}$alkoxy, hydroxy, halogen, trifluoromethyl, nitro, cyano, $C_{1-12}$carboxylic acyl or amino or aminocarbonyl optionally substituted by one or two $C_{1-6}$alkyl groups; or (when X is O). $R_5$ is selected from the class of carboxy, $C_{1-6}$alkoxycarbonyl or aminocarbonyl optionally substituted by one or two $C_{1-6}$alkyl groups; and, $R_6$ is hydrogen or $C_{1-6}$alkyl; or $R_5$ and $R_6$ together are $-CH_2-(CH_2)_n-Z-(CH_2)_m-$
wherein m and n are 0 to 2 such that m+n is 1 or 2 and Z is $CH_2$, O, S or NR wherein R is hydrogen, $C_{1-9}$alkyl, $C_{2-7}$alkanoyl, phenyl, $C_{1-4}$alkyl, naphthylcarbonyl, phenylcarbonyl or benzyl-carbonyl optionally substituted in the phenyl or naphthyl ring by one or two of $C_{1-6}$alkyl, $C_{1-6}$alkoxy or halogen or R is heteroarylcarbonyl;

X is oxygen or sulphur; or $R_5$, $R_6$, X and N together are tetrahydroisoquinolinone or tetrahydroisoquinolinthione optionally substituted in the phenyl ring as defined for R above;

the nitrogen-containing group in the 4-position being trans to the $R_3$ group when $R_3$ is hydroxy, $C_{1-4}$alkoxy or $C_{1-7}$acyloxy;

compounds as disclosed in PCT 87/00386 having the formula

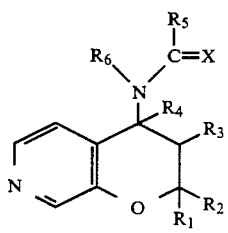

M and pharmaceutically acceptable salts thereof, wherein $R_1$ is hydrogen or alkyl; $R_2$ is alkyl or $R_1$ and $R_2$ are polymethylene; $R_3$ is hydrogen, hydroxy, alkoxy, acyloxy; $R_4$ is hydrogen or $R_3$ and $R_4$ are a bond; $R_5$ is hydrogen, optionally substituted alkyl, alkenyl, optionally substituted amino, optionally substituted aryl or heteroaryl, carboxy, alkoxycarbonyl or aminocarbonyl; $R_6$ is hydrogen or alkyl or $R_5$ and $R_6$ together are $-CH_2-(CH_2)_n-Z-(CH_2)_m-$, wherein m and n are 0 to 2, m+n is 1 or 2, Z is $CH_2$, O, S, NR; R is hydrogen, alkyl, alkanoyl, phenylalkyl, naphthylcarbonyl, phenylcarbonyl, benzylcarbonyl, or heteroaryl-carbonyl; X is O, S or $R_5$, $R_6$, X and N together are tetrahydroisoquinolinone or tetrahydroisoquinolinthione;

compounds as disclosed in EP 344,747 having the formula

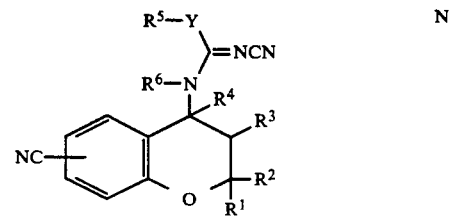

N wherein
$R^1$ and $R^2$ are each lower alkyl;
$R^3$ is hydroxy or acyloxy and $R^4$ is hydrogen; or
$R^3$ and $R^4$ are linked together to form a bond, and
(i) Y is $-S-$, $-O-$ or a group of the formula $$-\overset{R^7}{\underset{|}{N}}-$$

wherein
$R^7$ is hydrogen, acyl or lower alkyl which may have suitable substituent(s); and
$R^5$ and $R^6$ are each hydrogen or lower alkyl;
(ii) Y is as defined above; and
$R^5$ and $R^6$ are linked together to form lower alkylene; or
(iii) Y-$R^5$ is a heterocyclic group which may have suitable substituent(s); and
$R^6$ is hydrogen or lower alkyl;
and pharmaceutically acceptable salts thereof.

In carrying out the method of the present invention, the PCA may be administered to mammalian species, such as monkeys, dogs, cats, rats, humans, etc., to treat ulcerative gastrointestinal conditions. In methods for treating inflammatory conditions, the PCA's can be administered before, during or after antiinflammatory drug therapy alone or in combination with such drug.

The PCA may be administered systemically, such as orally, parenterally, intranasally or transdermally The PCA, alone or in combination with an antiinflammatory drug, may be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

With regard to such systemic formulations, single or divided doses of from about 5 to about 2500 mg, preferably from about 10 to 2000 mg/one to four times daily, may be administered in systemic dosage forms as described above for a period sufficient to reduce existing ulcerative conditions, or may be administered previous to and preferably concurrently with antiinflammatory drugs.

With regard to combinations of the PCA with anti-inflammatory agent, single or divided doses of from 5 to about 2500 mg of PCA, preferably 10 to 2000 mg of PCA, and from about 2 to about 2000 mg anti-inflammatory agent and preferably from about 5 to about 1500 mg anti-inflammatory agent, depending upon the type of anti-inflammatory agent employed, may be administered one to eight times daily.

It will be appreciated that all of the anti-inflammatory drugs disclosed herein are known for treating inflammation and/or pain and may be employed in dosage forms and amounts as disclosed in the Physicians' Desk Reference.

The preferred embodiments of this invention involve using compounds of the general formulae C, E, F or G. Compounds of formula C, E, F or G are useful in the present method where little or no antihypertensive action is desired. Such "selective" compounds are those potassium channel activators which have $IC_{50}$ (rat aorta) values greater than that of cromakalim. Preferably the $IC_{50}$ value is 10 times greater and more preferably 100 times greater than that of cromakalim. In other words, the preferred embodiments use compounds which preferably have 1/10 and more preferably 1/100 of the vasorelaxant activity of cromakalim. These include compounds of formula C where $R_7$ is (or compounds of formula E, F or G where $R_1$ is) aryl, especially substituted phenyl, arylalkyl, heteroaryl or heteroarylalkyl.

The term "ulcerative conditions of the gastrointestinal tract" as employed herein includes conditions such as gastric ulcers, duodenal ulcers, Crohn's disease, ulcerative colitis, irritable bowel syndrome, and inflammatory bowel disease.

Further, in accordance with the present invention, a new combination is provided which includes a PCA and an anti-inflammatory drug which may be employed in a weight ratio to each other of within the range of from about 0.01:1 to about 100:1, and preferably from about 0.5:1 to about 2:1.

The above combination may be employed to treat pain, joint swelling, and stiffness associated with rheumatoid arthritis or to treat diseases in the manner of known anti-inflammatory agents.

Anti-inflammatory drugs or agents which may be employed herein include, but are not limited to, aspirin, indomethacin, ibuprofen, meclofenamate, naproxen, phenylbutazone, piroxicam, and various cortcicosteroids including hydrocortisone, dexamethasone, and methylpredisolone.

EXAMPLE 1

Aspirin-Induced Gastric Erosions

Male Sprague-Dawley rats (150–350 g) were housed separately in cages with wire mesh floors that would allow fecal material to fall through. They were fasted overnight before the experiment and allowed free access to water. On each experiment day, the order of treatments was randomized. One hour after oral dosing with Vehicle (1% methyl cellulose—MO262, Sigma Chemical Co.) or the subject potassium channel activator (3S-trans)-N-(4-chlorophenyl)-N"-cyano-N'-(6-cyano-3,4-dihydro-3-hydroxy-2,2-dimethyl-2H-1-benzopyran-4-yl)guanidine (3, 10 or 30 mg/kg), rats were dosed with aspirin (200 mg/kg, p.o.) prepared in a 1% methyl cellulose vehicle. Three hours after receiving aspirin, each rat was sacrificed by $CO_2$ asphyxiation. The stomach was removed, slit open along its greater curvature, rinsed with normal saline, and examined under a 2.5X magnifying lens. The gastric erosions were counted and the total area of gastric erosion measured. The results are illustrated in FIG. 1 and Table 1 below. The left half of Table 1 summarizes the measured areas of gastric erosion in the four groups of rats: vehicle (mean±SEM=7.57+0.96 $mm^2$), the subject potassium channel activator (3 mg/kg; 5.31±1.22 $mm^2$), the subject potassium channel activator (10 mg/kg; 4.58±0.96 $mm^2$), and the subject potassium channel activator (30 mg/kg, 3.16±0.89 $mm^2$). The average lesion areas±SEM for vehicle and treatment groups are summarized in FIG. 1. The subject potassium channel activator induced reduction in gastric lesion area was statistically significant by analysis of variance (p=0.022). The right half of Table 1 shows the percent protection [i.e., ((7.57−lesion area)/7.75)×100] afforded by the subject potassium channel activator treatment compared to the average lesion area in the vehicle group. The dose producing a 50% reduction in aspirin-induced gastric lesion area (i.e., $ID_{50}$) was calculated to be 17.4 mg/kg, p.o. by regression analysis.

TABLE 1

| 11/13,14 & 12/5,6/1991 | | | | BMS 180,448 (3, 10 and 30 mg/kg, p.o., in 1% MC, 60 min before ASA @ 200 mg/kg, p.o., in 1% MC) | | | | |
|---|---|---|---|---|---|---|---|---|
| | Vehicle | BMS 3 mg/kg | BMS 10 mg/kg | BMS 30 mg/kg | | Vehicle % Pro | Dose 1% Pro | Dose 2% Pro | Dose 3% Pro |
| | 2.38 | 7.31 | 10.44 | 4.44 | | 68.6% | 3.4% | −37.9% | 41.3% |
| | 8.50 | 6.69 | 5.69 | 0.94 | | −12.3% | 11.6% | 24.8% | 87.6% |
| | 8.19 | 6.31 | 2.13 | 3.75 | | −8.2% | 16.6% | 71.9% | 50.5% |
| | 6.38 | 4.94 | 8.25 | 10.50 | | 15.7% | 34.7% | −9.0% | −38.7% |
| | 8.13 | 8.06 | 0.88 | 6.13 | | −7.4% | −6.5% | 88.4% | 19.0% |
| | 3.07 | 2.50 | 5.88 | 5.31 | | 59.4% | 67.0% | 22.3% | 29.8% |
| | 10.00 | 16.28 | 1.38 | 2.63 | | −32.1% | −115.1% | 81.8% | 65.3% |
| | 8.25 | 0.44 | 10.25 | 1.06 | | −9.0% | 94.2% | −35.4% | 86.0% |
| | 2.69 | 1.12 | 0.63 | 1.56 | | 64.5% | 85.2% | 91.7% | 79.4% |
| | 6.38 | 2.88 | 2.63 | 0.00 | | 15.7% | 61.9% | 65.3% | 100.0% |
| | 6.31 | 3.19 | 1.56 | 1.63 | | 16.6% | 57.9% | 79.4% | 78.5% |
| | 8.50 | 4.00 | 4.31 | 0.00 | | −12.3% | 47.2% | 43.1% | 100.0% |
| | 16.56 | | 5.56 | | | −118.8% | | 26.5% | |
| | 5.75 | | | | | 24.0% | | | |
| | 12.44 | | | | | −64.4% | | | |
| Mean | 7.57 | 5.31 | 4.58 | 3.16 | p = 0.022 by | 0.0% | 29.8% | 39.4% | 58.2% |
| SEM | 0.96 | 1.22 | 0.96 | 0.89 | ANOVA | 12.6% | 16.1% | 12.6% | 11.7% |

TABLE 1-continued

| 11/13,14 & 12/5,6/1991 | | | BMS 180,448 (3, 10 and 30 mg/kg, p.o., in 1% MC, 60 min before ASA @ 200 mg/kg, p.o., in 1% MC) | | | | |
|---|---|---|---|---|---|---|---|
| Vehicle | BMS 3 mg/kg | BMS 10 mg/kg | BMS 30 mg/kg | Vehicle % Pro | Dose 1% Pro | Dose 2% Pro | Dose 3% Pro |
| N 15 | 12 | 13 | 12 | | | | ID50 = 17.4 mg/kg, p.o. |

What is claimed is:

1. A method for preventing or treating ulcerative conditions of the gastrointestinal tract, in a mammalian species, which comprises administering to a mammalian species in need of such treatment an effective amount of a potassium channel activator.

2. The method as defined in claim 1 wherein the potassium channel activator is nicrorandil, minoxidil, a compound of the formula

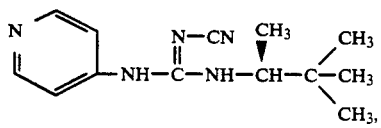

A known as pinacidil;

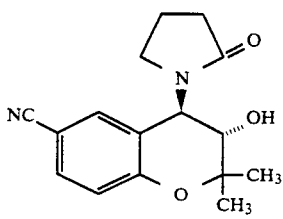

B known as cromakalim;

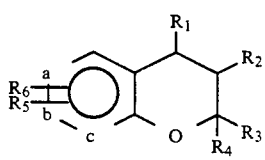

C wherein a, b, and c are all carbons or one of a, b and c can be nitrogen or —NO— and the others are carbons;

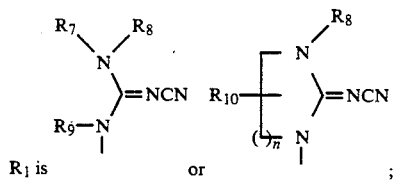

$R_1$ is or ;

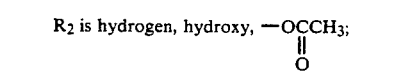

$R_2$ is hydrogen, hydroxy, —OCCH$_3$;
                                ‖
                                O $R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

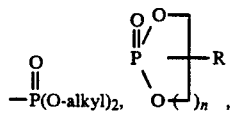

halogen, amino, substituted amino, O-alkyl, OCF$_3$, OCH$_2$CF$_3$, —OCOalkyl, —OCONRalkyl, —NR-COalkyl and NRCOOalkyl, NRCONR$_2$ wherein R in each of the above groups can be hydrogen, alkyl, aryl, arylalkyl, cycloalkyl, or (cycloalkyl)alkyl;

$R_6$ is selected from H, alkyl, OH, O-alkyl, amino, substituted amino, CN, and NO$_2$;

$R_7$ and $R_8$ are each independently selected from hydrogen, alkyl, alkenyl, aryl (including phenyl substituted with R' and R" as defined below), (heterocyclo)alkyl, heterocyclo, arylalkyl, cycloalkyl and (cycloalkyl)alkyl, substituted alkyl wherein the substituents include alkoxy, alkylthio and substituted amino, or $R_7$ and $R_8$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R_9$ and $R_{10}$ are selected from hydrogen, alkyl, alkenyl, aryl, arylalkyl, cycloalkyl or cycloalkyl; and n is 1, 2 or 3;

with the compound

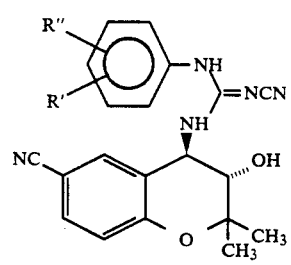

C'

(where R' and R" are independently hydrogen, cyano, alkyl, alkoxy, nitro, hydroxy, halo, haloalkyl, alkylthio, amino, —N(alkyl)$_2$, —NHalkyl or benzyloxy with the proviso that at least one of R' and R" is other than hydrogen) being preferred;

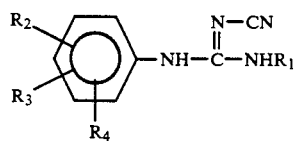

D and its possible tautomers

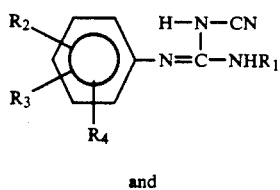

and

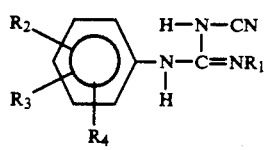

wherein $R_1$ is alkyl, alkenyl, alkynyl, haloalkyl, cycloalkyl, aryl, arylalkyl or cycloalkylalkyl;

$$R_2 \text{ is } -C\equiv N, -NO_2, -\overset{O}{\underset{\|}{C}}R_5, -\overset{O}{\underset{\|}{C}}-OR_5, -\overset{O}{\underset{\|}{C}}\text{-amino,}$$

$$-\overset{O}{\underset{\|}{C}}\text{-substituted amino, } CF_3 \text{ or } -\overset{(O)_m}{\underset{\|}{S}}-R_1;$$

$R_3$ and $R_4$ are each independently selected from $-R_2$, hydrogen, alkyl, alkenyl, alkynyl, haloalkyl, halo, alkoxy, —NHalkyl, —N-(alkyl)$_2$, —S-alkyl, —O-arylalkyl, —S-arylalkyl or —S-aryl, —O-aryl, —NHarylalkyl, or $R_2$ and $R_3$ taken together are a group which forms a ring with the two carbon atoms to which they are attached, which group is selected from $$-\overset{(O)_m}{\underset{\|}{S}}-(CH_2)_n-CH_2-, \quad -\overset{O}{\underset{\|}{C}}X(CH_2)_pCH_2-, \quad -\overset{O}{\underset{\|}{C}}-CH_2(CH_2)_pX-;$$

wherein
m = 1 or 2;
n = 1-3;
p = 0-2;
X is O, NR$_5$, CH$_2$; and,
R$_5$ is hydrogen or R$_1$;

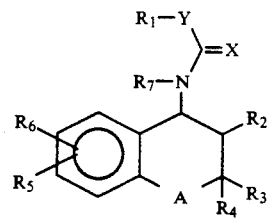

wherein A can be —CH$_2$—, —O—, —NR$_9$—, —S—, —SO— or —SO$_2$—, where R$_9$ is hydrogen or lower alkyl of 1 to 4 carbons;
wherein X is oxygen or sulfur;
Y is —NR$_8$, —O—, —S— or $$-\overset{R_{10}}{\underset{|}{C}H}-;$$

R$_1$ is aryl, arylalkyl, heterocyclo or (heterocyclo)alkyl;
R$_2$ is hydrogen, hydroxy, $$-\overset{O}{\underset{\|}{O}CCH_3};$$

R$_3$ and R$_4$ are each independently hydrogen, alkyl or arylalkyl, or, R$_3$ and R$_4$ taken together with the carbon atom to which they are attached form a 5- to 7-membered carbocyclic ring;
R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

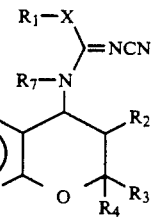

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;
R$_6$ is selected form H, alkyl, halo, OH, O-alkyl, amino and substituted amino;
R$_7$ and R$_8$ are each independently selected from hydrogen, alkyl, arylalkyl;
n is 1, 2 or 3; and,
R$_{10}$ is hydrogen, hydroxy, alkyl or O-alkyl;

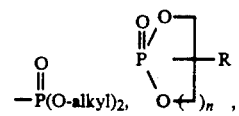

wherein a, b and c are all carbons or one of a, b and c can be nitrogen or —NO— and the others are carbons;
where X is oxygen or sulfur;
R$_1$ is selected from aryl, arylalkyl, (heterocyclo)alkyl, heterocyclo, cycloalkyl and (cycloalkyl)alkyl;
R$_2$ is hydrogen, hydroxy, $$-\overset{O}{\underset{\|}{O}CCH_3};$$

R$_3$ and R$_4$ are each independently hydrogen, alkyl or arylalkyl, or R$_3$ and R$_4$ taken together with the carbon atom to which they are attached form a 5- to 7-membered carbocyclic ring;
R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

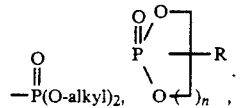

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

R$_6$ is selected from H, alkyl, OH, O-alkyl, amino, substituted amino, CN and NO$_2$;

R$_7$ is selected from hydrogen, alkyl, alkenyl, aryl, arylalkyl, cycloalkyl or cycloalkylalkyl; and, n is 1, 2 or 3; and,

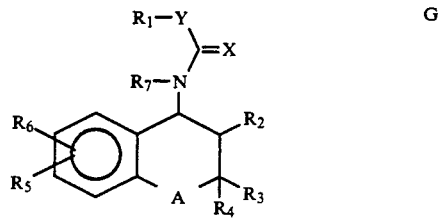

G wherein A can be —CH$_2$—, —O—, —NR$_9$—, —S—, —SO— or —SO$_2$—, where R$_9$ is hydrogen or lower alkyl of 1 to 4 carbons;

wherein X is oxygen or sulfur;

Y is —NR$_8$, —O—, —S— or

R$_1$ is aryl, arylalkyl, heterocyclo or (heterocyclo)alkyl;

R$_2$ is hydrogen, hydroxy,

R$_3$ and R$_4$ are each independently hydrogen, alkyl or arylalkyl, or R$_3$ and R$_4$ taken together with the carbon atom to which they are attached form a 5- to 7-membered carbocyclic ring;

R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

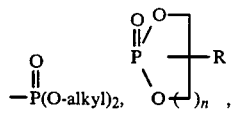

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl or haloalkyl;

R$_6$ is selected from H, alkyl, halo, OH, o-alkyl, amino and substituted amino, O-alkyl, OCOalkyl, OCONRalkyl, NRCOalkyl and NRCOOalkyl, NRCON(R)$_2$ wherein R in each of the above groups can be hydrogen, alkyl, aryl, arylalkyl, cycloalkyl, (cycloalkyl)alkyl or haloalkyl;

R$_7$ and R$_8$ are each independently selected from hydrogen, alkyl, arylalkyl;

or R$_1$ and R$_8$, or R$_1$ and R$_7$, or R$_7$ and R$_8$ taken together can form a 5- to 7-membered saturated or unsaturated ring, which may further include an aryl group fused to 2 carbon atoms of such 5- to 7-membered ring;

n is 1, 2 or 3; and,

R$_{10}$ is hydrogen, hydroxy, alkyl or O-alkyl.

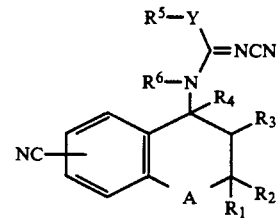

H wherein

R$^1$ and R$^2$ are each lower alkyl;

R$^3$ is hydroxy or acyloxy and R$^4$ is hydrogen or R$^3$ and R$^4$ are linked together to form a bond, and (i) Y is —S—, —O— or a group of the formula:

wherein R$^7$ is hydrogen, acyl or lower alkyl which may have suitable substituent(s), and R$^5$ and R$^6$ are each hydrogen or lower alkyl, (ii) Y is as defined above, and R$^5$ and R$^6$ are linked together to form lower alkylene, or (iii) Y-R$^5$ is a heterocyclic group which may have suitable substituent(s), and R$^6$ is hydrogen or lower alkyl

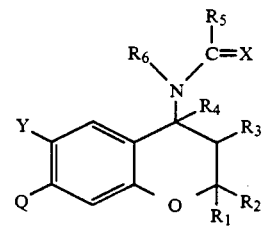

J and salts thereof, wherein one of R$_1$ and R$_2$ is hydrogen or C$_{1-4}$alkyl and the other is C$_{1-4}$alkyl or R$_1$ and R$_2$ together are C$_{2-5}$-polymethylene;

either R$_3$ is hydrogen, hydroxy, C$_{1-6}$alkoxy or C$_{1-7}$acyloxy and R$_4$ is hydrogen or R$_3$ and R$_4$ together are a bond;

R$_5$ is hydrogen, C$_{1-6}$alkyl optionally substituted by halogen, hydroxy, C$_{1-6}$alkoxy, C$_{1-6}$alkoxycarbonyl, carboxy or amino optionally substituted by one or two independent C$_{1-6}$alkyl groups, or C$_{2-6}$alkenyl, amino optionally substituted by a C$_{1-6}$alkyl or C$_{1-6}$alkenyl group or by a C$_{1-6}$alkanoyl group optionally substituted by up to three halo atoms, by a phenyl group optionally substituted by C$_{1-6}$alkyl, C$_{1-6}$alkoxy or halogen, or aryl or heteroaryl, either being optionally substituted by one or more groups or atoms selected from the class of C$_{1-6}$alkyl, C$_{1-6}$alkoxy, hydroxy, halogen, trifluoromethyl, nitro, cyano, C$_{1-12}$carboxylic acyl, or amino or aminocarbonyl optionally substituted by one or two C$_{1-6}$alkyl groups and R$_6$ is hydrogen or C$_{1-6}$alkyl, or $R_5$ and $R_6$ together are —$CH_2$—($CH_2$)$_n$—$Z$—($CH_2$)$_m$— wherein m and n are 0 to 2 such that m+n is 1 or 2 and Z is $CH_2$, O, S or NR wherein R is hydrogen, $C_{1-9}$alkyl, $C_{2-7}$alkanoyl, phenyl $C_{1-4}$alkyl, naphthylcarbonyl, phenylcarbonyl or benzylcarbonyl optionally substituted in the phenyl or naphthyl ring by one or two of $C_{1-6}$alkyl, $C_{1-6}$alkoxy or halogen; mono- or bi-cyclic-heteroarylcarbonyl;

X is oxygen or sulphur;

Y and Q are electron withdrawing groups; and the nitrogen-containing group in the 4-position being trans to the $R_3$ group when $R_3$ is hydroxy, $C_{1-6}$alkoxy or $C_{1-7}$acyloxy;

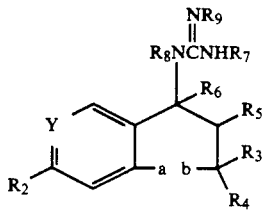

K wherein
 a and b together form an —O— or —$CH_2$— linkage or a bond;
 either Y is N and $R_2$ is hydrogen; or
 Y is C—$R_1$;
wherein
 either one of $R_1$ and $R_2$ is hydrogen and the other is nitro, cyano, halo, $CF_3$, formyl, aldoxime, $CF_3O$, $NO_2$—CH=CH—, NC—CH=CH—;
 a group $R_xX$-wherein $R_x$ is $C_{1-6}$alkyl, aryl or heteroaryl either of which may be optionally substituted by one, two or three of $C_{1-4}$alkyl, $C_{1-4}$alkoxy, nitro, halo, $CF_3$ and cyano; and X is C=O, O.C=O, C=O.O, CHOH, SO, $SO_2$, O.SO, O.$SO_2$, CONH, O.CONH, C=S, O.C=S, C=S.O, CH.SH, SONH, $SO_2NH$, O.SONH, O.$SO_2NH$, CO—CH=CH, C=NHOH, C=$NNH_2$;
 or a group $R_yR_zNZ$— wherein $R_y$ and $R_z$ are independently hydrogen or $C_{1-6}$alkyl and Z is C=O, SO or $SO_2$; or
 $R_1$ is a $C_{3-8}$cycloalkyl group or a $C_{1-6}$alkyl group optionally substituted by a group which is hydroxy, $C_{1-6}$alkoxy, amino optionally substituted by one or two $C_{1-6}$alkyl groups, $C_{1-7}$alkanoylaino, $C_{3-8}$cycloalkyloxy or $C_{3-8}$cycloalkylamino; and $R_2$ is hydrogen; or
 one of $R_1$ and $R_2$ is nitro, cyano or $C_{1-3}$alkylcarbonyl and the other is a different group selected from nitro cyano, halo, $C_{1-3}$alkylcarbonyl, methoxy or amino optionally substituted by one or two $C_{1-6}$alkyl or by $C_{2-7}$alkanoyl;
 either one of $R_3$ and $R_4$ is hydrogen or $C_{1-4}$alkyl and the other is $C_{1-4}$alkyl; or
 $R_3$ and $R_4$ together are $C_{2-5}$polymethylene;
 either $R_5$ is hydrogen, hydroxy, $C_{1-6}$alkoxy or $C_{1-7}$acyloxy; and
 $R_6$ is hydrogen; or
 $R_5$ and $R_6$ together are a bond;
 either $R_7$ is hydrogen, $C_{1-6}$alkyl, $C_{3-6}$cycloalkyl, $C_{2-6}$alkenyl or $C_{2-6}$alkynyl; and
 $R_8$ is hydrogen or $C_{1-6}$alkyl; or
 $R_7$ and $R_8$ together are $C_{2-4}$polymethylene;

$R_9$ is CN, $NO_2$ $COR_{10}$ wherein $R_{10}$ is $C_{1-3}$alkyl, $NH_2$, NH($C_{1-3}$alkyl), $CF_3$ or phenyl optionally substituted as defined for $R_x$; and the $R_8N(NR_9)NHR_7$ moiety is trans to the $R_5$ group when $R_5$ is hydroxy, $C_{1-6}$alkoxy or $C_{1-7}$acyloxy;

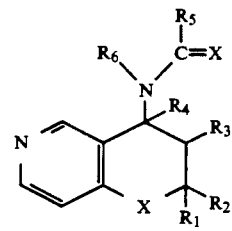

L wherein
 one of $R_1$ and $R_2$ is hydrogen or $C_{1-4}$alkyl and the other is $C_{1-4}$alkyl or $R_1$ and $R_2$ together are $C_{2-5}$polymethylene;
 either $R_3$ is hydrogen, hydroxy, $C_{1-6}$alkoxy or $C_{1-6}$acyloxy and $R_4$ is hydrogen or $R_3$ and $R_4$ together are a bond;
 $R_5$ is hydrogen; $C_{1-6}$alkyl optionally substituted by up to three halo atoms, by hydroxy, $C_{1-4}$alkoxy, $C_{1-6}$alkoxycarbonyl, carboxy, or amino optionally substituted by one or two independent $C_{1-6}$alkyl groups or disubstituted by $C_{4-5}$poly-methylene, $C_{2-6}$alkenyl; amino optionally substituted by a $C_{1-6}$alkyl or $C_{1-6}$alkenyl group or by a $C_{1-6}$alkanoyl group optionally substituted by up to three halo atoms, by a phenyl group optionally substituted by $C_{1-6}$alkyl, $C_{1-6}$alkoxy or halogen; or aryl or heteroaryl, either being optionally substituted by one or more groups or atoms selected from the class of $C_{1-6}$alkyl, $C_{1-6}$alkoxy, hydroxy, halogen, trifluoromethyl, nitro, cyano, $C_{1-12}$carboxylic acyl or amino or aminocarbonyl optionally substituted by one or two $C_{1-6}$alkyl groups; or (when X is O). $R_5$ is selected from the class of carboxy, $C_{1-6}$alkoxycarbonyl or aminocarbonyl optionally substituted by one or two $C_{1-6}$alkyl groups; and,
 $R_6$ is hydrogen or $C_{1-6}$alkyl; or
 $R_5$ and $R_6$ together are —$CH_2$—($CH_2$)$_n$—$Z$—($CH_2$)$_m$— wherein m and n are 0 to 2 such that m+n is 1 or 2 and Z is $CH_2$, O, S or NR wherein R is hydrogen, $C_{1-8}$alkyl, $C_{2-7}$alkanoyl, phenyl, $C_{1-4}$alkyl, naphthylcarbonyl, phenylcarbonyl or benzylcarbonyl optionally substituted in the phenyl or naphthyl ring by one or two of $C_{1-6}$alkyl, $C_{1-6}$alkoxy or halogen or R is heteroarylcarbonyl;

X is oxygen or sulphur; or $R_5$, $R_6$, X and N together are tetrahydroisoquinolinone or tetrahydroisoquinolinthione optionally substituted in the phenyl ring as defined for R above;

the nitrogen-containing group in the 4-position being trans to the $R_3$ group when $R_3$ is hydroxy, $C_{1-4}$alkoxy or $C_{1-7}$acyloxy;

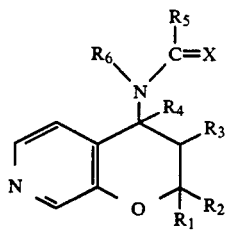

M and pharmaceutically acceptable salts thereof, wherein $R_1$ is hydrogen or alkyl; $R_2$ is alkyl or $R_1$ and $R_2$ are polymethylene; $R_3$ is hydrogen, hydroxy, alkoxy, acyloxy; $R_4$ is hydrogen or $R_3$ and $R_4$ are a bond; $R_5$ is hydrogen, optionally substituted alkyl, alkenyl, optionally substituted amino, optionally substituted aryl or heteroaryl, carboxy, alkoxycarbonyl or aminocarbonyl; $R_6$ is hydrogen or alkyl or $R_5$ and $R_6$ together are —CH$_2$—(CH$_2$)$_n$—Z—(CH$_2$)$_m$—, wherein m and n are 0 to 2, m+n is 1 or 2, Z is CH$_2$, O, S, NR; R is hydrogen, alkyl, alkanoyl, phenyl-alkyl, naphthylcarbonyl, phenylcarbonyl, benzylcarbonyl, or heteroaryl-carbonyl; X is O, S or $R_5$, $R_6$, X and N together are tetrahydroisoquinolinone or tetrahydroisoquinolin-thione;

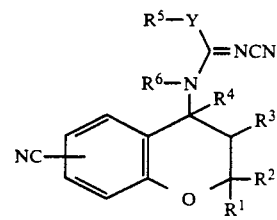

N wherein
$R^1$ and $R^2$ are each lower alkyl;
$R^3$ is hydroxy or acyloxy and $R^4$ is hydrogen; or
$R^3$ and $R^4$ are linked together to form a bond, and
(i) Y is —S—, —O— or a group of the formula

wherein
$R^7$ is hydrogen, acyl or lower alkyl which may have suitable substituent(s); and
$R^5$ and $R^6$ are each hydrogen or lower alkyl;
(ii) Y is as defined above; and
$R^5$ and $R^6$ are linked together to form lower alkylene; or
(iii) Y-$R^5$ is a heterocyclic group which may have suitable substituent(s); and
$R^6$ is hydrogen or lower alkyl;
and pharmaceutically acceptable salts thereof.

3. The method of claim 1 wherein the potassium channel activator has little or no vasorelaxant activity in normal tissue.

4. The method of claim 3 wherein said potassium channel activator is selected from C where $R_7$ is aryl, arylalkyl, heteroaryl and heteroaryl(alkyl), E, F or G where $R_1$ is aryl, arylalkyl, heteroaryl or heteroaryl(alkyl).

5. The method of claim 4 wherein the aryl group for $R_7$ in C or $R_1$ in E, F or G is substituted phenyl.

6. The method of claim 5 wherein the potassium channel activator is

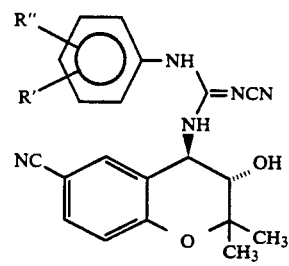

C'

(where R' and R" are independently hydrogen, cyano, alkyl, alkoxy, nitro, hydroxy, halo, haloalkyl, alkylthio, amino, —N(alkyl)$_2$, —NHalkyl or benzyloxy with the proviso that at least one of R' and R" is other than hydrogen) being preferred;

7. The method of claim 6 wherein the potassium channel activator is

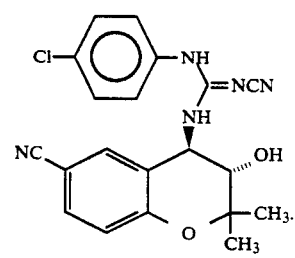

8. The method of claim 1 wherein said ulcerative condition of the gastrointestinal tract is induced by the administration of one or more antiinflammatory drugs.

9. The method of claim 8 wherein said potassium channel activator is administered concurrently with the antiinflammatory drug.

10. The method of claim 9 wherein said concurrent administration is provided by a single, combination dosage form.

11. A method for preventing or treating an inflammatory condition without causing gastrointestinal ulcers, in a mammalian species, which comprises administering to a mammalian species in need of such treatment an effective amount of a potassium channel activator concurrently with a therapeutically effective amount of an anti-inflammatory agent.

12. The method of claim 11 wherein said potassium channel activator is nicorandil, minoxidil, a compound of the formula

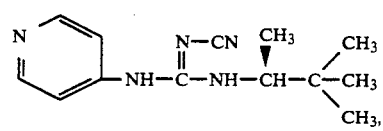

A known as pinacidil;

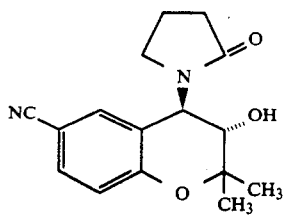

known as cromakalim;

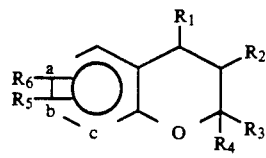

wherein a, b, and c are all carbons or one of a, b and c can be nitrogen or —NO— and the others are carbons;

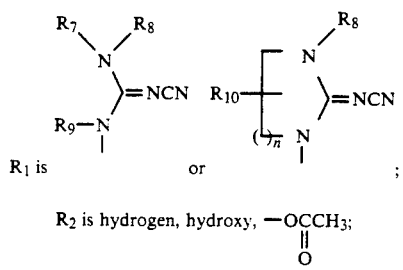

$R_2$ is hydrogen, hydroxy, —OCCH$_3$;
$\underset{O}{\|}$ $R_2$ is hydrogen, hydroxy, $R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

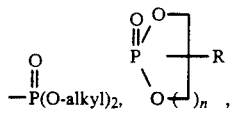

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

$R_6$ is selected from H, alkyl, OH, O-alkyl, amino, substituted amino, CN, and NO$_2$;

$R_7$ and $R_8$ are each independently selected from hydrogen, alkyl, alkenyl, aryl (including phenyl substituted with R' and R" as defined below), (heterocyclo)alkyl, heterocyclo, arylalkyl, cycloalkyl and (cycloalkyl)alkyl, substituted alkyl wherein the substituents include alkoxy, alkylthio and substituted amino, or $R_7$ and $R_8$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R_9$ and $R_{10}$ are selected from hydrogen, alkyl, alkenyl, aryl, arylalkyl, cycloalkyl or cycloalkyl; and n is 1, 2 or 3;

with the compound

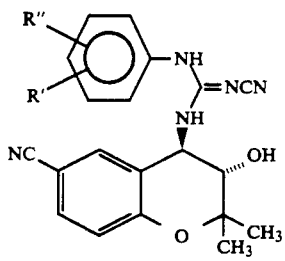

(where R' and R' are independently hydrogen, cyano, alkyl, alkoxy, nitro, hydroxy, halo, haloalkyl, alkylthio, amino, —N(alkyl)$_2$, —NHalkyl or benzyloxy with the proviso that at least one of R' and R" is other than hydrogen) being preferred;

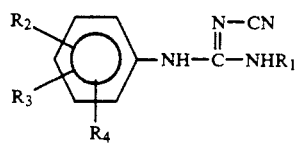

and its possible tautomers

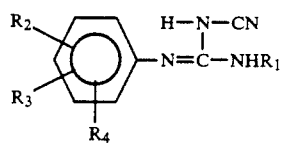

and

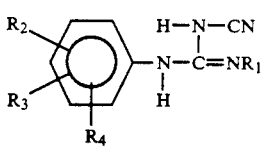

wherein $R_1$ is alkyl, alkenyl, alkynyl, haloalkyl, cycloalkyl, aryl, arylalkyl or cycloalkylalkyl;

$R_2$ is $-C\equiv N$, $-NO_2$, $-\overset{O}{\overset{\|}{C}}R_5$, $-\overset{O}{\overset{\|}{C}}-OR_5$, $-\overset{O}{\overset{\|}{C}}$-amino, $-\overset{O}{\overset{\|}{C}}$-substituted amino, CF$_3$ or $-\overset{(O)_m}{\overset{\|}{S}}-R_1$;

$R_3$ and $R_4$ are each independently selected from —R$_2$, hydrogen, alkyl, alkenyl, alkynyl, haloalkyl, halo, alkoxy, —NHalkyl, —N-(alkyl)$_2$, —S-alkyl, —O-arylalkyl, —S-arylalkyl or —S-aryl, —O-aryl, —NHarylalkyl, or $R_2$ and $R_3$ taken together are a group which forms a ring with the two carbon atoms to which they are attached, which group is selected from

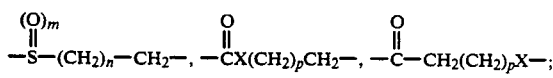

wherein
m = 1 or 2;
n = 1-3;
p = 0-2;
X is O, NR$_5$, CH$_2$; and,
R$_5$ is hydrogen or R$_1$;

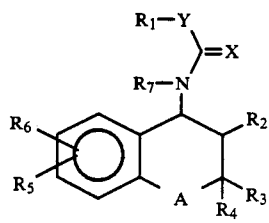

E wherein A can be —CH$_2$—, —O—, —NR$_9$—, —S—, —SO— or —SO$_2$—, where R$_9$ is hydrogen or lower alkyl of 1 to 4 carbons;
wherein X is oxygen or sulfur;
Y is —NR$_8$, —O—, —S— or

R$_1$ is aryl, arylalkyl, heterocyclo or (heterocyclo)alkyl;
R$_2$ is hydrogen, hydroxy,

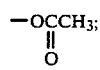

R$_3$ and R$_4$ are each independently hydrogen, alkyl or arylalkyl, or, R$_3$ and R$_4$ taken together with the carbon atom to which they are attached form a 5- to 7-membered carbocyclic ring;
R$_5$ is selected form H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

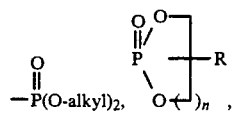

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;
R$_6$ is selected from H, alkyl, halo, OH, O-alkyl, amino and substituted amino;
R$_7$ and R$_8$ are each independently selected from hydrogen, alkyl, arylalkyl;
n is 1, 2 or 3; and,
R$_{10}$ is hydrogen, hydroxy, alkyl or O-alkyl;

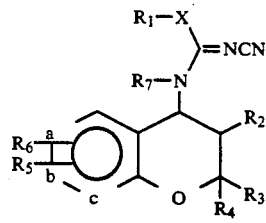

F wherein a, b and c are all carbons or one of a, b, and c can be nitrogen or —NO— and the others are carbons; where X is oxygen or sulfur;
R$_1$ is selected from aryl, arylalkyl, (heterocyclo)alkyl, heterocyclo, cycloalkyl and (cycloalkyl)alkyl;
R$_2$ is hydrogen, hydroxy,

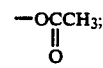

R$_3$ and R$_4$ are each independently hydrogen, alkyl or arylalkyl, or R$_3$ and R$_4$ taken together with the carbon atoms to which they are attached form a 5- to 7-membered carbocyclic ring;
R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

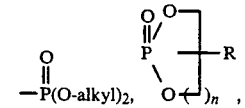

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;
R$_6$ is selected from H, alkyl, OH, O-alkyl, amino, substituted amino, CN and NO$_2$;
R$_7$ is selected from hydrogen, alkyl, alkenyl, aryl, arylalkyl, cycloalkyl or cycloalkylalkyl; and,
n is 1, 2 or 3; and,

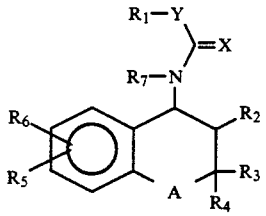

G wherein A can be —CH$_2$—, —O—, —NR$_9$—, —S—, —SO— or —SO$_2$—, where R$_9$ is hydrogen or lower alkyl of 1 to 4 carbons;
wherein X is oxygen or sulfur;
Y is —NR$_8$, —O—, —S— or

$R_1$ is aryl, arylalkyl, heterocyclo or (heterocyclo)alkyl;

$R_2$ is hydrogen, hydroxy, $$-O\underset{\underset{O}{\|}}{C}CH_3;$$

$R_3$ and $R_4$ are each independently hydrogen, alkyl or arylalkyl, or $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —$NO_2$, —COR, —COOR, —CONHR, —$CONR_2$, —$CF_3$, S-alkyl, —SOalkyl, —$SO_2$alkyl, $$-P(O\text{-alkyl})_2, \quad \overset{O}{\underset{\|}{P}}\overset{O^-}{\underset{\diagdown}{\diagup}}{\overset{R}{\underset{O{+}}{}}}_n,$$

halogen, amino, substituted amino, O-alkyl, $OCF_3$, $OCH_2CF_3$, —OCOalkyl, —OCONRalkyl, —NRCOalkyl and NRCOOalkyl, $NRCONR_2$ wherein R in each of the above groups can be hydrogen, alkyl, aryl, arylalkyl, cycloalkyl, or (cycloalkyl)alkyl or haloalkyl;

$R_6$ is selected from H, alkyl, halo, OH, o-alkyl, amino and substituted amino, O-alkyl, OCOalkyl, OCONRalkyl, NRCOalkyl and NRCOOalkyl, $NRCON(R)_2$ wherein R in each of the above groups can be hydrogen, alkyl, aryl, arylalkyl, cycloalkyl, (cycloalkyl)alkyl or haloalkyl;

$R_7$ and $R_8$ are each independently selected from hydrogen, alkyl, arylalkyl;

or $R_1$ and $R_8$, or $R_1$ and $R_7$, or $R_7$ and $R_8$ taken together can form a 5- to 7-membered saturated or unsaturated ring, which may further include an aryl group fused to 2 carbon atoms of such 5- to 7-membered ring;

n is 1, 2 or 3; and, $R_{10}$ is hydrogen, hydroxy, alkyl or O-alkyl.

H wherein $R^1$ and $R^2$ are each lower alkyl;

$R^3$ is hydroxy or acyloxy and $R^4$ is hydrogen or $R^3$ and $R^4$ are linked together to form a bond, and (i) Y is —S—, —O— or a group of the formula:

$$-\overset{R^7}{\underset{|}{N}}-$$

wherein $R^7$ is hydrogen, acyl or lower alkyl which may have suitable substituent(s), and $R^5$ and $R^6$ are each hydrogen or lower alkyl, (ii) Y is as defined above, and $R^5$ and $R^6$ are linked together to form lower alkylene, or (iii) Y-$R^5$ is a heterocyclic group which may have suitable substituent(s), and $R^6$ is hydrogen or lower alkyl

J and salts thereof, wherein one of $R_1$ and $R_2$ is hydrogen or $C_{1-4}$alkyl and the other is $C_{1-4}$alkyl or $R_1$ and $R_2$ together are $C_{2-5}$-polymethylene;

either $R_3$ is hydrogen, hydroxy, $C_{1-6}$alkoxy or $C_{1-7}$acyloxy and $R_4$ is hydrogen or $R_3$ and $R_4$ together are a bond;

$R_5$ is hydrogen, $C_{1-6}$alkyl optionally substituted by halogen, hydroxy, $C_{1-6}$alkoxy, $C_{1-6}$alkoxycarbonyl, carboxy or amino optionally substituted by one or two independent $C_{1-6}$alkyl groups, or $C_{2-6}$alkenyl, amino optionally substituted by a $C_{1-6}$alkyl or $C_{1-6}$alkenyl group or by a $C_{1-6}$alkanoyl group optionally substituted by up to three halo atoms, by a phenyl group optionally substituted by $C_{1-6}$alkyl, $C_{1-6}$alkoxy or halogen, or aryl or heteroaryl, either being optionally substituted by one or more groups or atoms selected from the class of $C_{1-6}$alkyl, $C_{1-6}$alkoxy, hydroxy, halogen, trifluoromethyl, nitro, cyano, $C_{1-12}$carboxylic acyl, or amino or aminocarbonyl optionally substituted by one or two $C_{1-6}$alkyl groups and $R_6$ is hydrogen or $C_{1-6}$alkyl, or $R_5$ and $R_6$ together are —$CH_2$—($CH_2$)$_n$—Z—($CH_2$)$_m$— wherein m and n are 0 to 2 such that m+n is 1 or 2 and Z is $CH_2$, O, S or NR wherein R is hydrogen, $C_{1-9}$alkyl, $C_{2-7}$alkanoyl, phenyl $C_{1-4}$alkyl, naphthylcarbonyl, phenylcarbonyl or benzylcarbonyl optionally substituted in the phenyl or naphthyl ring by one or two of $C_{1-6}$alkyl, $C_{1-6}$alkoxy or halogen; mono- or bi-cyclic-heteroarylcarbonyl;

X is oxygen or sulphur;

Y and Q are electron withdrawing groups; and the nitrogen-containing group in the 4-position being trans to the $R_3$ group when $R_3$ is hydroxy, $C_{1-6}$alkoxy or $C_{1-7}$acyloxy;

K wherein a and b together form an —O— or —$CH_2$— linkage or a bond;

either Y is N and $R_2$ is hydrogen; or

Y is C-$R_1$;

wherein either one of $R_1$ and $R_2$ is hydrogen and the other is nitro, cyano, halo, $CF_3$, formyl, aldoxime, $CF_3O$, $NO_2$—CH=CH—, NC—CH=CH—;

a group $R_xX$—wherein $R_x$ is $C_{1-6}$alkyl, aryl or heteroaryl either of which may be optionally substituted by one, two or three of $C_{1-4}$alkyl, $C_{1-4}$alkoxy, nitro, halo, $CF_3$ and cyano; and X is C=O, O.C=O, C=O.O, CHOH, SO, $SO_2$, O.SO, O.$SO_2$, CONH, O.CONH, C=S, O.C=S, C=S.O, CH.SH, SONH, $SO_2$NH, O.SONH, O.$SO_2$NH, CO—CH=CH, C=NHOH, C=NNH$_2$;

or a group $R_yR_zNZ$— wherein $R_y$ and $R_z$ are independently hydrogen or $C_{1-6}$alkyl and Z is C=O, SO or $SO_2$; or $R_1$ is a $C_{3-8}$cycloalkyl group or a $C_{1-6}$alkyl group optionally substituted by a group which is hydroxy, $C_{1-6}$alkoxy, amino optionally substituted by one or two $C_{1-6}$alkyl groups, $C_{1-7}$alkanoylaino, $C_{3-8}$cycloalkyloxy or $C_{3-8}$cycloalkylamino; and $R_2$ is hydrogen; or one of $R_1$ and $R_2$ is nitro, cyano or $C_{1-3}$alkylcarbonyl and the other is a different group selected from nitro Cyano, halo, $C_{1-3}$alkylcarbonyl, methoxy or amino optionally substituted by one or two $C_{1-6}$alkyl or by $C_{2-7}$alkanoyl;

either one of $R_3$ and $R_4$ is hydrogen or $C_{1-4}$alkyl and the other is $C_{1-4}$alkyl; or $R_3$ and $R_4$ together are $C_{2-5}$polymethylene;

either $R_5$ is hydrogen, hydroxy, $C_{1-6}$alkoxy or $C_{1-7}$acyloxy; and $R_6$ is hydrogen; or $R_5$ and $R_6$ together are a bond;

either $R_7$ is hydrogen, $C_{1-6}$alkyl, $C_{3-6}$cycloalkyl, $C_{2-6}$alkenyl or $C_{2-6}$alkynyl; and $R_8$ is hydrogen or $C_{1-6}$alkyl; or $R_7$ and $R_8$ together are $C_{2-4}$polymethylene;

$R_9$ is CN, $NO_2$, $COR_{10}$ wherein $R_{10}$ is $C_{1-3}$alkyl, $NH_2$, NH($C_{1-3}$alkyl). $CF_3$ or phenyl optionally substituted as defined for $R_x$; and the $R_8N(NR_9)NHR_7$ moiety is trans to the $R_5$ group when $R_5$ is hydroxy, $C_{1-6}$alkoxy or $C_{1-7}$acyloxy;

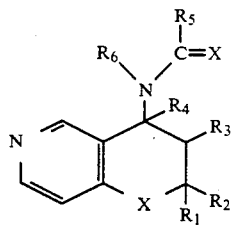  L wherein
one of $R_1$ and $R_2$ is hydrogen or $C_{1-4}$alkyl and the other is $C_{1-4}$alkyl or $R_1$ and $R_2$ together are $C_{2-5}$polymethylene;

either $R_3$ is hydrogen, hydroxy, $C_{1-6}$alkoxy or $C_{1-6}$acyloxy and $R_4$ is hydrogen or $R_3$ and $R_4$ together are a bond;

$R_5$ is hydrogen; $C_{1-6}$alkyl optionally substituted by up to three halo atoms, by hydroxy, $C_{1-4}$alkoxy, $C_{1-6}$alkoxycarbonyl, carboxy, or amino optionally substituted by one or two independent $C_{1-6}$alkyl groups or disubstituted by $C_{4-5}$polymethylene, $C_{2-6}$alkenyl; amino optionally substituted by a $C_{1-6}$alkyl or $C_{1-6}$alkenyl group or by a $C_{1-6}$alkanoyl group optionally substituted by up to three halo atoms, by a phenyl group optionally substituted by $C_{1-6}$alkyl, $C_{1-6}$alkoxy or halogen; or aryl or heteroaryl, either being optionally substituted by one or more groups or atoms selected from the class of $C_{1-6}$alkyl, $C_{1-6}$alkoxy, hydroxy, halogen, trifluoromethyl, nitro, cyano, $C_{1-12}$carboxylic acyl or amino or aminocarbonyl optionally substituted by one or two $C_{1-6}$alkyl groups; or (when X is O). $R_5$ is selected from the class of carboxy, $C_{1-6}$alkoxycarbonyl or aminocarbonyl optionally substituted by one or two $C_{1-6}$alkyl groups; and, $R_6$ is hydrogen or $C_{1-6}$alkyl; or $R_5$ and $R_6$ together are —CH$_2$—(CH$_2$)$_n$—Z—(CH$_2$)$_m$— wherein m and n are 0 to 2 such that m+n is 1 or 2 and Z is CH$_2$, O, S or NR wherein R is hydrogen, $C_{1-8}$alkyl, $C_{2-7}$alkanoyl, phenyl, $C_{1-4}$alkyl, naphthylcarbonyl, phenylcarbonyl or benzylcarbonyl optionally substituted in the phenyl or naphthyl ring by one or two of $C_{1-6}$alkyl, $C_{1-6}$alkoxy or halogen or R is heteroarylcarbonyl;

X is oxygen or sulphur; or $R_5$, $R_6$, X and N together are tetrahydroisoquinolinone or tetrahydroisoquinolinthione optionally substituted in the phenyl ring as defined for R above;

the nitrogen-containing group in the 4-position being trans to the $R_3$ group when $R_3$ is hydroxy, $C_{1-4}$alkoxy or $C_{1-7}$acyloxy;

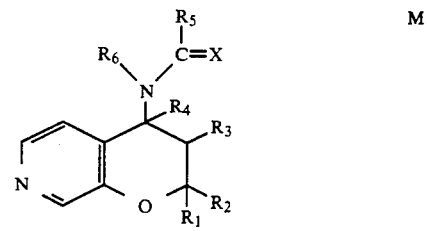  M and pharmaceutically acceptable salts thereof, wherein $R_1$ is hydrogen or alkyl; $R_2$ is alkyl or $R_1$ and $R_2$ are polymethylene; $R_3$ is hydrogen, hydroxy, alkoxy, acyloxy; $R_4$ is hydrogen or $R_3$ and $R_4$ are a bond; $R_5$ is hydrogen, optionally substituted alkyl, alkenyl, optionally substituted amino, optionally substituted aryl or heteroaryl, carboxy, alkoxycarbonyl or aminocarbonyl; $R_6$ is hydrogen or alkyl or $R_5$ and $R_6$ together are —CH$_2$—(CH$_2$)$_n$—Z—(CH$_2$)$_m$—, wherein m and n are 0 to 2, m+n is 1 or 2, Z is CH$_2$, O, S, NR; R is hydrogen, alkyl, alkanoyl, phenyl-alkyl, naphthylcarbonyl, phenylcarbonyl, benzylcarbonyl, or heteroaryl-carbonyl; X is O, S or $R_5$, $R_6$, X and N together are tetrahydroisoquinolinone or tetrahydroisoquinolin-thione;

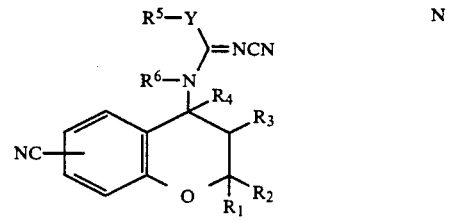  N wherein
$R^1$ and $R^2$ are each lower alkyl;
$R^3$ is hydroxy or acyloxy and $R^4$ is hydrogen; or
$R^3$ and $R^4$ are linked together to form a bond, and
(i) Y is —S—, —O— or a group of the formula

wherein

R⁷ is hydrogen, acyl or lower alkyl which may have suitable substituent(s); and

R⁵ and R⁶ are each hydrogen or lower alkyl;

(ii) Y is as defined above; and

R⁵ and R⁶ are linked together to form lower alkylene; or (iii) Y-R⁵ is a heterocyclic group which may have suitable substituent(s); and R⁶ is hydrogen or lower alkyl; and pharmaceutically acceptable salts thereof.

13. The method of claim 11 wherein the potassium channel activator has little or no vasorelaxant activity in normal tissue.

14. The method of claim 11 wherein said potassium channel activator is selected from C where R₇ is aryl, arylalkyl, heteroaryl and heteroaryl(alkyl), E, F or G where R₁ is aryl, arylalkyl, heteroaryl or heteroaryl(alkyl).

15. The method of claim 11 wherein the aryl group for R₇ in C or R₁ in E, F or G is substituted phenyl.

16. The method of claim 11 wherein the potassium channel activator is

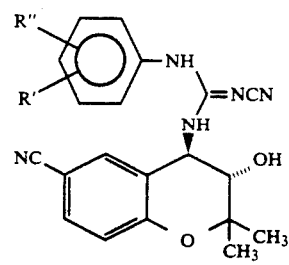

where R' and R" are independently hydrogen, cyano, alkyl, alkoxy, nitro, hydroxy, halo, haloalkyl, alkylthio, amino, —N(alkyl)₂, —NHalkyl or benzyloxy with the proviso that at least one of R' and R" is other than hydrogen.

17. The method of claim 11 wherein the potassium channel activator is

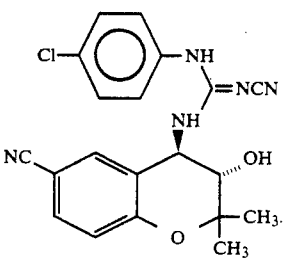

* * * * *